United States Patent
Tal et al.

(10) Patent No.: US 10,918,516 B2
(45) Date of Patent: Feb. 16, 2021

(54) INTRAUTERINE DEVICE WITH CONTROLLED COPPER ION ELUTION

(71) Applicant: SEBELA VLC LIMITED, Hamilton (BM)

(72) Inventors: Michael Tal, Savyon (IL); Bob H. Katz, Los Gatos, CA (US); Scott M. Russell, San Jose, CA (US)

(73) Assignee: SEBELA VLC LIMITED, Hamilton (BM)

( * ) Notice: Subject to any disclaimer, the term of this patent is extended or adjusted under 35 U.S.C. 154(b) by 971 days.

(21) Appl. No.: 15/441,539

(22) Filed: Feb. 24, 2017

(65) Prior Publication Data

US 2017/0165103 A1 Jun. 15, 2017

Related U.S. Application Data

(63) Continuation-in-part of application No. 14/289,530, filed on May 28, 2014, now Pat. No. 10,188,546.

(60) Provisional application No. 61/890,714, filed on Oct. 14, 2013.

(51) Int. Cl.
*A61F 6/14* (2006.01)
*A61F 6/18* (2006.01)

(52) U.S. Cl.
CPC .............. *A61F 6/144* (2013.01); *A61F 6/18* (2013.01); *Y10T 29/49826* (2015.01)

(58) Field of Classification Search
CPC ....... A61F 6/144; A61F 6/18; Y10T 29/49826
See application file for complete search history.

(56) References Cited

U.S. PATENT DOCUMENTS

| 662,716 A | 11/1900 | Gaedeke |
| 3,407,806 A | 10/1968 | Hulka |
| 3,492,990 A | 2/1970 | Clarke |
| 3,678,927 A | 7/1972 | Soichet |
| 3,750,661 A | 8/1973 | Knoch |
| 3,750,662 A | 8/1973 | Lerner |

(Continued)

FOREIGN PATENT DOCUMENTS

| CN | 87210467 | 4/1988 |
| CN | 202096333 | 1/2012 |

(Continued)

OTHER PUBLICATIONS

Supplementary European Search Report for Application No. 14853521. 4, dated May 2, 2017, 9 pages.

(Continued)

*Primary Examiner* — John C Hong
(74) *Attorney, Agent, or Firm* — Merchant & Gould P.C.

(57) ABSTRACT

A method of manufacturing an intrauterine device (IUD) for contraception that has a desired copper elution rate is described. The method may involve selecting an elongate shape memory member comprising a first metal having a first galvanic potential, selecting at least one attachment member comprising a second metal having a second galvanic potential that is different from the first galvanic potential, attaching the attachment member(s) to the shape memory member, and shaping the shape memory member to form a frame of the intrauterine contraceptive device. The first metal and the second metal are specifically selected as materials for the shape memory member and the attachment member(s), in order to achieve the desired copper elution rate.

23 Claims, 5 Drawing Sheets

(56) References Cited

U.S. PATENT DOCUMENTS

| | | |
|---|---|---|
| 3,789,838 A | 2/1974 | Fournier et al. |
| 3,902,483 A | 9/1975 | Place et al. |
| 3,911,911 A | 10/1975 | Scommegna |
| 3,973,560 A | 8/1976 | Emmett |
| 3,996,933 A | 12/1976 | Gutnick |
| 4,136,695 A | 1/1979 | Dafoe |
| 4,762,130 A | 8/1988 | Fogarty et al. |
| 5,507,725 A | 4/1996 | Savage et al. |
| RE35,636 E | 10/1997 | Diaz et al. |
| 5,785,053 A | 7/1998 | Macandrew et al. |
| 6,119,696 A | 9/2000 | Turin |
| 6,152,943 A | 11/2000 | Sawhney |
| 6,588,429 B1 | 7/2003 | Wildemeersch |
| 6,709,667 B1 | 3/2004 | Lowe et al. |
| 6,742,520 B1 | 6/2004 | Wildemeersch |
| 7,506,650 B2 | 3/2009 | Lowe et al. |
| 7,591,268 B2 | 9/2009 | Lowe et al. |
| 7,621,276 B2 | 11/2009 | Tal et al. |
| 7,661,429 B2 | 2/2010 | Jutila |
| 7,669,601 B2 | 3/2010 | Tal |
| 8,079,364 B2 | 12/2011 | Lowe et al. |
| 8,181,653 B2 | 5/2012 | Tal et al. |
| 8,435,205 B2 | 8/2013 | Arora et al. |
| 8,573,222 B2 | 11/2013 | Weintraub |
| 8,662,081 B2 | 3/2014 | Tal et al. |
| 8,700,120 B2 | 4/2014 | Koblish |
| 9,016,280 B2 | 4/2015 | Tal et al. |
| 9,089,418 B2 | 7/2015 | Tal et al. |
| 9,180,039 B2 | 11/2015 | Tal et al. |
| 9,180,040 B2 | 11/2015 | Tal et al. |
| 9,265,652 B2 | 2/2016 | Tal et al. |
| 9,427,351 B2 | 8/2016 | Tal et al. |
| 9,492,311 B2 | 11/2016 | Tal et al. |
| 9,510,088 B2 | 11/2016 | Tal et al. |
| 9,610,191 B2 | 4/2017 | Tal |
| 10,159,596 B2 | 12/2018 | Tal et al. |
| 10,166,141 B2 | 1/2019 | Tal et al. |
| 10,188,546 B2 | 1/2019 | Tal et al. |
| 2004/0163651 A1 | 8/2004 | Nikolchev et al. |
| 2005/0187561 A1 | 8/2005 | Lee-Sepsick et al. |
| 2005/0240211 A1 | 10/2005 | Sporri |
| 2005/0274384 A1 | 12/2005 | Tran et al. |
| 2008/0047563 A1 | 2/2008 | Tal et al. |
| 2008/0216842 A1 | 9/2008 | Acedo |
| 2010/0300452 A1 | 12/2010 | Tal et al. |
| 2011/0061659 A1 | 3/2011 | Cruzada et al. |
| 2011/0162656 A1 | 7/2011 | Jutila et al. |
| 2011/0166508 A1 | 7/2011 | Lyytikainen et al. |
| 2011/0172593 A1 | 7/2011 | Lyyikainen et al. |
| 2012/0097172 A1 | 4/2012 | Tal et al. |
| 2012/0111338 A1 | 5/2012 | Weitraub |
| 2013/0014762 A1 | 1/2013 | Deckman et al. |
| 2013/0068234 A1 | 3/2013 | Pandit |
| 2013/0152942 A1 | 6/2013 | Lyytikainen et al. |
| 2013/0211321 A1 | 8/2013 | Dubois |
| 2013/0213406 A1 | 8/2013 | Frankenne et al. |
| 2013/0217960 A1 | 8/2013 | Arora et al. |
| 2013/0220338 A1 | 8/2013 | Lyyikainen et al. |
| 2013/0255695 A1 | 10/2013 | Jutila et al. |
| 2013/0319424 A1 | 12/2013 | Weintraub |
| 2014/0041667 A1 | 2/2014 | Cammack |
| 2014/0048073 A1 | 2/2014 | Tal et al. |
| 2014/0048074 A1 | 2/2014 | Tal et al. |
| 2014/0076328 A1 | 3/2014 | Lyytikainen et al. |
| 2015/0101613 A1 | 4/2015 | Tal et al. |
| 2015/0107598 A1 | 4/2015 | Tal et al. |
| 2015/0305922 A1 | 10/2015 | Tal et al. |
| 2015/0313753 A1 | 11/2015 | Tal et al. |
| 2015/0335465 A1 | 11/2015 | Tal et al. |
| 2016/0058608 A1 | 3/2016 | Tal et al. |
| 2016/0058609 A1 | 3/2016 | Tal et al. |
| 2016/0331579 A1 | 11/2016 | Tal et al. |
| 2017/0056237 A1 | 3/2017 | Tal et al. |
| 2017/0202701 A1 | 7/2017 | Tal et al. |
| 2019/0125576 A1 | 5/2019 | Tal et al. |

FOREIGN PATENT DOCUMENTS

| | | |
|---|---|---|
| CN | 203138640 | 8/2013 |
| CN | 203970514 | 12/2014 |
| EP | 2327381 | 6/2011 |
| WO | WO198000536 | 4/1980 |
| WO | WO1990009158 | 8/1990 |
| WO | WO 2006042561 | 4/2006 |
| WO | WO2007136965 | 11/2007 |
| WO | WO2008048764 | 4/2008 |
| WO | WO2010036721 | 4/2010 |
| WO | WO2012027090 | 3/2012 |
| WO | WO2014028499 | 2/2014 |

OTHER PUBLICATIONS

International Search Report and Written Opinion for Application No. PCT/US2014/049392, dated Mar. 31, 2015, 6 pages.

INTRAUTERINE DEVICE WITH CONTROLLED COPPER ION ELUTION

CROSS-REFERENCE TO RELATED APPLICATION

The present application is a continuation-in-part of U.S. patent application Ser. No. 14/289,530, entitled "Intrauterine Device with Controlled Copper Ion Elution," filed May 28, 2014, now U.S. Pat. No. 10,188,546, which claims priority to U.S. Provisional Patent Application No. 61/890,714, entitled "Intrauterine Device with Controlled Copper Ion Elution," filed on Oct. 14, 2013. The full disclosures of the above-listed patent applications are hereby incorporated by reference herein.

FIELD OF THE INVENTION

The present invention relates to medical devices. More specifically, the invention relates to intrauterine devices for contraception.

BACKGROUND

An intrauterine device (IUD) is a small, often T-shaped device, containing copper or hormone (e.g., levonorgestrel), which is inserted into the uterus to provide long-acting, reversible contraception. As of 2007, IUDs are the most widely used form of reversible contraception, with more than 180 million users worldwide. IUDs typically are one of two types—copper or hormonal.

Copper IUDs primarily work by disrupting sperm motility and damaging sperm so that the sperm are prevented from joining with an egg. Copper acts as a spermicide within the uterus, increasing levels of copper ions, prostaglandins, and white blood cells within the uterine and tubal fluids. The increased copper ions in the cervical mucus inhibit the sperm's motility and viability, preventing sperm from traveling through a thickened cervical mucus and/or destroying it as it passes through. Copper IUDs have a typical first-year contraceptive success rate greater than 98 percent.

Most copper IUDs have a plastic T-shaped frame that is wound with pure electrolytic copper wire and/or has copper collars (sleeves). The arms of the frame hold the IUD in place near the top of the uterus. The Paragard® intrauterine copper contraceptive device (www.paragard.com) and the generic TCU 380A are currently the most common copper IUDs. Copper IUDs can typically be implanted for up to 10 years.

The mechanism of action of a copper IUD is essentially a predictable electrochemical process of corrosion, driven by the IUD's immersion in the uterine fluid. Over time, the copper element (wires, beads, tubes, etc.) corrodes and releases copper ions. Typically, the release rate is governed by the surface area and volume of copper, the chemistry (especially pH) of the uterine fluid, and the specific composition and surface properties of the copper elements. The frame of the IUD on which the copper is attached is typically made of a flexible, non-corrosive polymer. Since typical polymers are not electrochemically active, they do not influence the ion release rate of the copper elements. Therefore, the copper ion release characteristics of a typical plastic-frame IUD are strictly governed by the amount, preparation and configuration of the copper itself. One challenge with copper IUDs has been that increased effectiveness typically means increased amounts of copper on the IUD, and increased amounts of copper typically lead to increased side effects, primarily increased menstrual and intermenstrual bleeding, and increased pelvic pain. Balancing effectiveness with minimization of side effects has been a continuing challenge for making copper IUDs.

One advantage of the copper IUD is its ability to provide emergency contraception up to five days after unprotected sex. It is generally known as the most effective form of emergency contraception available. Another advantage is that it contains no hormones, so it can be used while breast feeding, and fertility returns quickly after removal. Lastly, copper IUDs have been shown to be clinically effective for up to 10 years of continuous use. Disadvantages include the possibility of heavier menstrual periods and more painful menstrual cramping in some women.

A hormonal IUD, such as the Mirena® Levonorgestrel-releasing intrauterine system (www.mirena-us.com), uses the controlled release of a hormonal contraceptive such as Levonorgestrel (a progestin). The hormonal contraceptive released from a hormonal IUD prevents ovulation from occurring. The hormone also thickens the cervical mucus so that sperm cannot reach the fallopian tubes. Hormonal IUDs can typically be implanted for up to 5 years.

Hormonal IUDs do not increase bleeding as copper-containing IUDs do. Instead, they can often reduce menstrual bleeding or prevent menstruation altogether, and thus they are sometimes used as a treatment for menorrhagia (heavy menstrual bleeding). Hormonal IUDs have common side effects, however. The most common side effects with levonorgestrel IUDs are hormone-related effects, such as headaches, nausea, breast tenderness, depression and cyst formation.

Based on effectiveness and the types of side effects, copper IUDs are preferable for many women. Although currently available copper IUDs are very effective, it would still be advantageous to have improved copper IUDs. For example, it would be advantageous to have copper IUDs that were very effective but had minimal side effects.

BRIEF SUMMARY

Disclosed herein are various embodiments of an improved copper IUD. Generally, the described embodiments provide an IUD with a desirable (or "controlled") release rate of copper ions. Different embodiments may be configured with different copper ion release rates. For example, a particular copper ion release rate may be identified to provide a desired balance between IUD effectiveness and reduced side effects, compared to currently available devices.

In one aspect of the present application, an intrauterine contraceptive device may include a frame comprising a first metal having a first galvanic potential and at least one metallic member coupled with the frame, the at least one metallic member comprising a second metal having a second galvanic potential different from the first galvanic potential. In some embodiments, the first galvanic potential may be more anodic than the second galvanic potential. In alternative embodiments, the first galvanic potential may be more cathodic than the second galvanic potential.

In some embodiments, the frame may be made entirely of metal. Alternatively, the frame may be made partially of metal and partially of a non-metallic substance. For example, the first metal may in some embodiments be Nitinol. The second metal may be copper. In some embodiments, for example, the metallic members are multiple copper sleeves disposed around the frame at various locations. Some embodiments include the combination of the first metal being Nitinol and the second metal being copper.

In embodiments where the second metal is copper, the first galvanic potential and the second galvanic potential may be configured to achieve approximately a desired copper elution rate of the at least one metallic member. In all of these embodiments, the non-metallic substance may be a polymer, a silicone rubber or other engineered polymer plastic, for example. Optionally, the device may further include a retrieval string attached to one end of the metal frame.

In another aspect of this disclosure, a method of preventing conception may involve advancing an intrauterine contraceptive device into a uterus, where the intrauterine device includes a frame comprising a first metal having a first galvanic potential, and at least one metallic member coupled with the frame, comprising a second metal having a second galvanic potential different from the first galvanic potential. In some embodiments, the second metal may be copper, and the first and second galvanic potentials may be configured to achieve approximately a desired copper ion elution rate. In some embodiments, the first metal may be Nitinol, and advancing the contraceptive device into the uterus may involve advancing a distal end of an introducer device through a cervix, into the uterus, and advancing the contraceptive device out of the distal end, thus allowing the Nitinol of the frame to expand to contact a wall of the uterus.

In yet another aspect of the disclosure, a method of manufacturing an IUD for contraception that has a desired copper elution rate may involve: selecting an elongate shape memory member comprising a first metal having a first galvanic potential; selecting at least one attachment member comprising a second metal having a second galvanic potential that is different from the first galvanic potential; attaching the attachment member(s) to the shape memory member; and shaping the shape memory member to form a frame of the intrauterine contraceptive device. The first metal and the second metal may be specifically selected as materials for the shape memory member and the at least one attachment member, in order to achieve the desired copper elution rate.

In some embodiments, the shape memory member may be a wire. Merely by way of example, the first material may be Nitinol, stainless steel, titanium, cobalt-based alloys, tantalum, platinum, gold, silver, or MP35N. In one embodiment, for example, the first metal is Nitinol, and the second metal is copper. Some embodiments may include multiple copper sleeves, which may be attached to the frame, for example, by passing the multiple copper sleeves over the shape memory member. In such an embodiment, the method may also include positioning the multiple sleeves along the shape memory member at different positions before or after shaping the shape memory member. The attachment member(s) may have any of a number of different forms, such as but not limited to sleeves, wires, ribbons, coils, tubes and beads.

In some embodiments, the first galvanic potential is more anodic than the second galvanic potential. Alternatively, the first galvanic potential may be more cathodic than the second galvanic potential. In some embodiments, the frame is made entirely of the first metal. In other embodiments, the frame is made partially of the first metal and partially of a non-metallic substance. For example, the frame may include a non-rigid material, such as but not limited to a flexible polymer thread, a polyester thread, a nylon thread or other biocompatible fabric. Optionally, the method may also include attaching a retrieval string to a bottom portion of the frame.

In one embodiments, shaping the shape memory member may involve forming the frame to include: a bottom loop; a middle portion comprising two parts of the elongate shape memory member extending upward from the bottom loop; multiple twists in the middle portion, forming a spring portion; two bends in the elongate shape memory member at a location above the multiple twists, where the elongate member crosses over itself; a first arm extending from a first bend of the two bends; a second arm extending from a second bend of the two bends; a first end loop at an end of the first arm; and a second end loop at an end of the second arm, where the first end loop and the second end loop in the elongate shape memory member comprise tissue contact surfaces.

In another aspect of this application, a method of manufacturing an IUD for contraception that has a desired copper elution rate may involve: selecting a wire comprising a first metal having a first galvanic potential; selecting at least one attachment member comprising a second metal having a second galvanic potential that is different from the first galvanic potential; attaching the at least one attachment member to the wire; and shaping the wire to form a frame. The shaping step may result in a frame that has: a bottom loop; a middle portion; multiple twists in the middle portion; two bends in the elongate shape memory member at a location above the multiple twists in the middle portion, where the elongate member crosses over itself; two arms extending from the two bends; a first end loop at an end of one of the two arms; and a second end loop at an end of the other of the two arms.

These and other aspects and embodiments will be described in further detail below, in reference to the attached drawing figures.

DETAILED DESCRIPTION

The mechanism of action of a copper IUD is essentially a predictable electrochemical process of corrosion, driven by the IUD's immersion in the uterine fluid. Over time, the copper elements of the IUD (copper wires, beads, tubes, or the like) corrode and release copper ions. For a given IUD, the copper ion release rate can be measured using standard laboratory tests in simulated uterine fluid (SUF). Typically, the release rate is governed by the surface area and volume of copper, the chemistry (especially pH) of the SUF, and the specific composition and surface properties of the copper elements. In currently available IUDs, the primary driver influencing the copper release rate is the amount of exposed copper surface area. In other words, to achieve a higher copper ion release rate, an IUD would typically have an increased copper surface area, which generally means the IUD will contain more copper overall.

Figure 1:
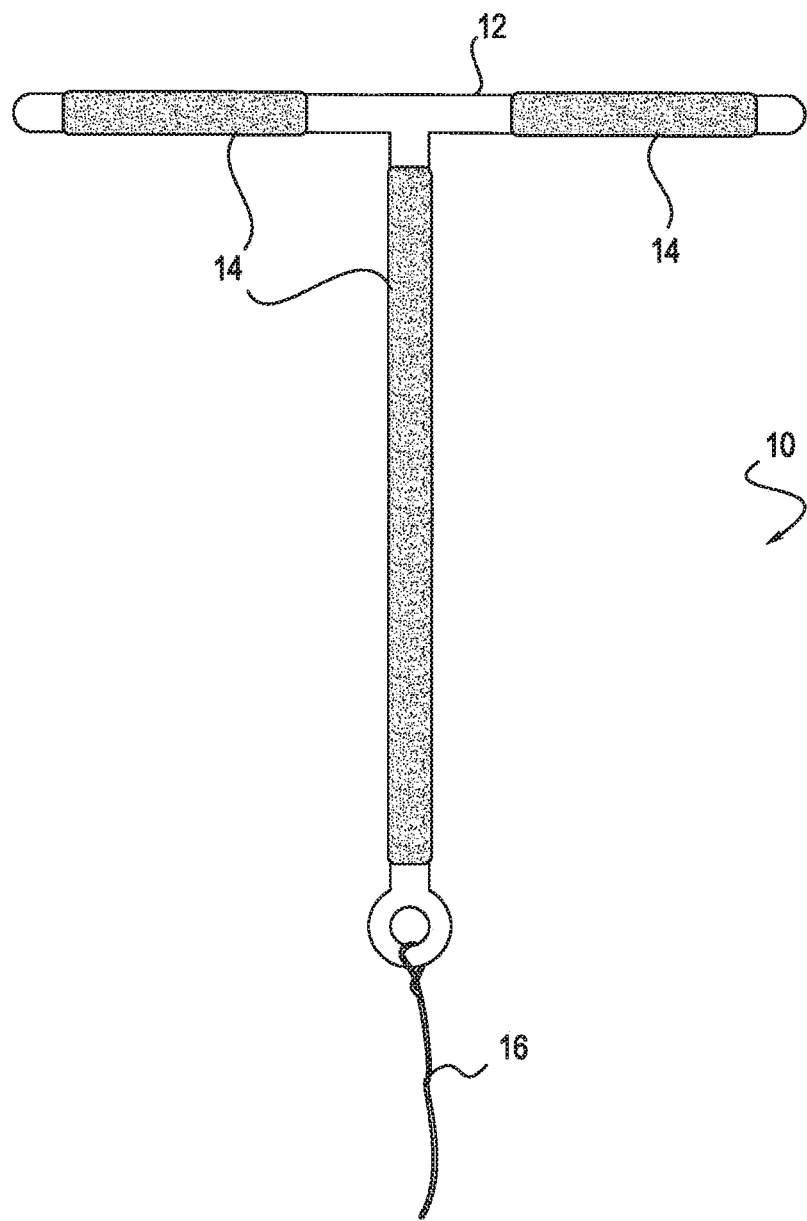
FIG. 1 is a front view of a prior art, T-shaped, copper IUD with a plastic support structure.

Referring now to FIG. 1, a typical, prior art, T-shaped, copper IUD 10 is illustrated. The IUD 10 includes a frame 12, copper sleeves 14 disposed around the frame 12 in three areas, and a retrieval string 16. The frame 12 is typically made of a flexible polymer and is often T-shaped for positioning in the uterus. Since typical polymers are not electrochemically active, they do not influence the ion release rate of the copper elements 14. Therefore, the copper ion release characteristics are strictly governed by the amount of surface area of the copper sleeves 14 themselves.

Galvanic corrosion is an electrochemical process in which one metal corrodes preferentially to another when both metals are in electrical contact and immersed in an electrolyte. The strength of this electrical potential between two metals or alloys is called the galvanic potential. The galvanic reaction can be exploited for positive benefit. For example, a galvanic potential between dissimilar metals can be used in primary batteries to generate an electrical voltage. The measured voltage is representative of the transfer of charged metal ions from one of the metals (the anode) to the other (the cathode). The stronger the galvanic effect between the two metals, the higher the transfer rate of ions from the anode to the cathode.

Figure 2:
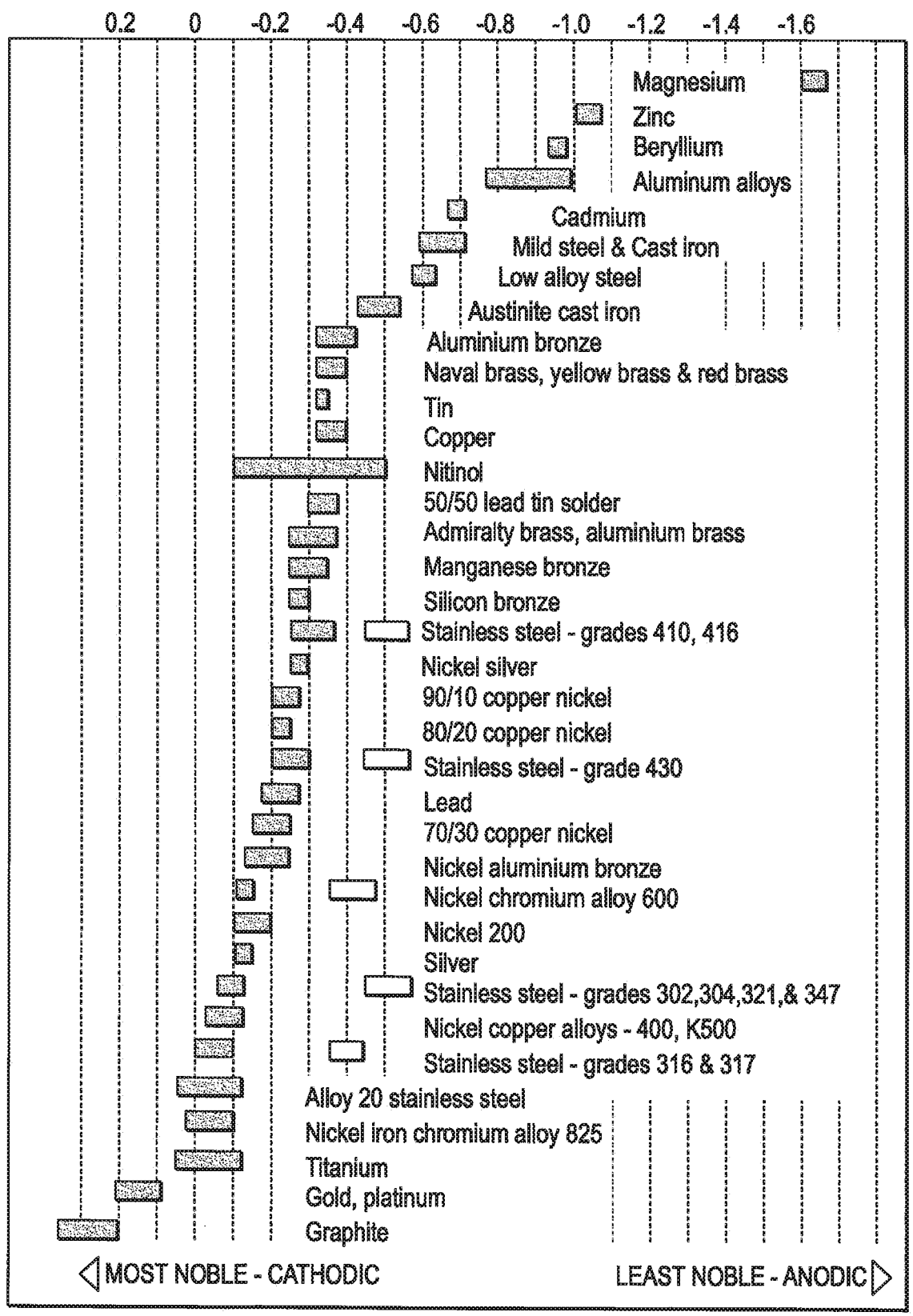
FIG. 2 is a bar graph illustrating a galvanic series for a number of common metals and alloys.

To determine the galvanic potential between two metals, we use a galvanic series, an example of which is illustrated in FIG. 2. In a galvanic series, metals are ranked by the electrical potential they develop in a given electrolyte against a standard reference electrode—i.e., their galvanic potential versus the reference electrode. The relative position of two metals on such a series determines which metal will be the anode and which will be the cathode (if they are put in contact in an appropriate electrolyte). The magnitude of the distance between the two metals on the galvanic series will determine the strength of the galvanic potential between them. A specific galvanic series can be determined for any metals or alloys of interest, tested in a specific electrolyte (e.g., SUF) at an appropriate pH.

Figure 3:
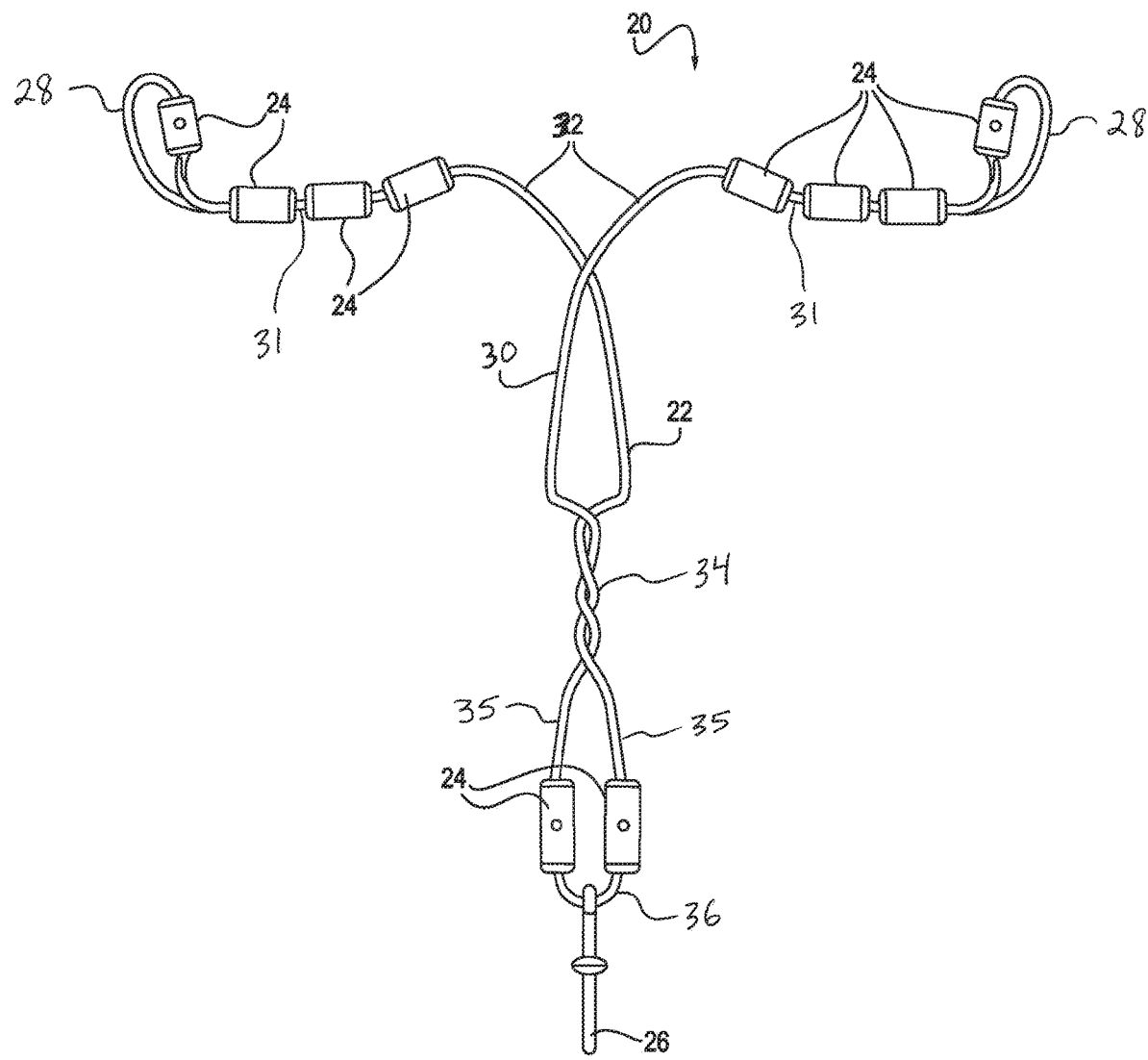
FIG. 3 is a front view of a copper IUD with a metal frame, according to one embodiment.

Referring now to FIG. 3, in one embodiment, an IUD 20 may include a metal frame 22 (or "shape memory member"), multiple copper sleeves 24 (or "copper elements"), and a retrieval string 26. This embodiment of the IUD 20, as well as other, alternative embodiments, is described in further detail in pending U.S. patent application Ser. No. 13/795,940, entitled "Intrauterine Contraceptive Device," filed Mar. 12, 2013, which is hereby incorporated by reference in its entirety. In this embodiment, the shape memory member 22 is generally made of a wire or wire-like material, and the copper sleeves 24 are generally tubular or partially tubular structures. In alternative embodiments, however, the shape memory member 22 and/or the sleeves 24 may take any of a number of different forms. For example, in one embodiment, the shape memory member 22 may be configured more like a flat ribbon that a cylindrical wire. In other embodiments, the sleeves 24 may be replaced by any other suitable attachment members, such as balls, coatings, clamps, tape or the like. Thus, the sleeves 24 are merely one example of a type of attachment member that might be used in forming the IUD 20.

In various embodiments, the elongate shape memory member 22 may have a two-dimensional (i.e., predominantly flat) configuration, as shown, or may have a more three dimensional (i.e., slightly bent out of plane) configuration. The elongate shape memory member 22 may include a loop portion 36 at the bottom (or "vertex") of the IUD 20, two generally parallel portions 35 extending vertically upward from the loop portion 36, multiple twists 34, a middle portion, two bends 32 that form the shape memory member 22 into two, approximately oppositely directed arms 31, and two tissue contact surfaces (or "end points") 28 at the ends of the two arms 31. The copper sleeves 24 are disposed around the shape memory member 22 at multiple locations, such as near each of the tissue contact surfaces 28, along the arms 31 between the bends 32 and the tissue contact surfaces 28, and at or near the loop portion 36. Different numbers and positions of the copper sleeves 24 may be provided in different alternative embodiments.

In this embodiment, the bottom loop portion 36 does not form any turns of a spring structure. Instead, to generate resilience in the arms 31 of the IUS 20, this embodiment includes twists the 34 between the parallel portions 35 and the middle portion 30. Twists 34 may be formed when the two portions 35 of the elongate member 22 cross each other more than once in a longitudinally extending helix containing multiple turns that run in series from closer to the loop portion 36 upward, until the arms diverge again from the twisted portion 34. FIG. 3 shows three twists 34. However, other numbers of twists (e.g., 1-5, 6-10, greater than 10) are also possible. In this embodiment, the twists 34 act as the "spring portion" to confer laterally directed pressure to tissue contact surfaces 28.

It may be desirable to be able to easily modify the properties of the elongate member 22. For example, the anatomical dimensions or characteristics of the uterus or medical conditions of a patient may call for adjustments to the outward force produced by the IUD 20. In such applications, the location of the twists 34 along the shape memory member 22, the number of the twists 34, and/or the tightness of the twists 34 may be used to provide variability in the properties of the device 20. For example, increasing the number of twists 34 may increase the stiffness of the elongate member 22, and decreasing the number of twists 34 may decrease the stiffness of the elongate member 22. For another example, increasing the tightness of the twists 34 may increase the stiffness of the elongate member 22. Decreasing the tightness of the twists 34 may decrease the stiffness of the elongate member 22. Moving the twists 34 upward along the shape memory member 22 may increase the stiffness of the elongate member 22, and moving the twists downward along the shape memory member 22 may decrease the stiffness of the elongate member 22. With the device of FIG. 3, a variety of differently configured devices can be made available to physicians to apply in the appropriate circumstances. The variability provided by the twists 34 also allows much easier and more continuous customization of properties by merely modifying the nature of the twists 34, rather than the thickness or material of the wire used to for the shape memory member 22 itself to produce similar variations in properties. Wires come in standard sizes and materials, and if some intermediate is desired, the expense can make producing such a modified device impractical. Controlling properties of the device with the properties of the twists 34 resolves this issue.

According to various embodiments, the galvanic effect can be exploited in the copper IUD 20 by coupling the copper elements 24 to the metal frame 22 or other metal structure. The material of the metal frame 22 or other elongate shape memory structure may be chosen to achieve a desired galvanic effect between itself and the copper elements 24. In one embodiment, for example, the frame 22 may be made of Nitinol (see FIG. 3, on which Nitinol and copper are depicted). In other embodiments, however, any of a number of other suitable biocompatible metals (or combinations of metals) may be selected for making the frame 22. In various embodiments, the type of material selected for the frame 22, the characteristics of the material (thickness, for example), the overall size of the IUD 20 (and thus the amount of the material used to make the frame 22), and/or other characteristics of the frame 22 may be specifically selected to provide a particular copper elution rate. Similarly, the type of size, number, positioning, and/or other factors pertaining to the copper sleeves 24 may be specifically selected to provide a particular embodiment with a particular copper elution rate. In other words, any of a number of characteristics of the frame 22 and/or the sleeves 24, such as but not limited to their materials, may be selected to provide a desired copper elution rate.

For the sake of comparison, a "baseline" copper ion elution rate may be defined as one in which there is no galvanic effect present (e.g., copper on a polymer frame, as in prior art IUDs). If the metal frame 22 (or other metallic structure) is selected to have a galvanic potential more anodic than the galvanic potential of the copper sleeves 24 (lower on the galvanic series), then the electrochemical driving force would be toward the copper sleeves 24, thereby reducing the copper ion release rate relative to the baseline. Alternatively, if the metal frame 22 or structure that has a galvanic potential more cathodic than the copper sleeves 24 (higher on the galvanic series), then the electrochemical driving force would be away from the copper sleeve 24, thereby increasing the copper ion release rate relative to the baseline. The greater the difference between the materials on the galvanic series, the more significant the decrease or increase in copper ion release rate. The galvanic potential is also related to the relative surface areas of the anode and the cathode, so the surface area ratio between the frame 22 and the copper sleeves 24 may also be selected to achieve a desired ion release rate.

In such a way, the material of the frame 22 and/or other elements in contact with the copper elements 24 may be selected to control the galvanic potential between the frame 22 and the copper 24, thereby allowing specificity, control and optimization of the ion release rate. This may have a number of advantages. In some embodiments, the IUD 20 may achieve a copper release rate comparable or identical to that of a currently available (i.e., prior art) IUD with a lower amount (i.e., less surface area) of copper, by coupling the copper 24 with the metal frame 22 that is more cathodic than the copper 24. The smaller surface area of the copper 24 may help reduce copper-related side effects, compared to prior art copper IUDs. Alternatively, in other embodiments, the IUD 20 may be configured to release copper ions at a rate similar or identical to that of a currently available copper IUD but for a longer period of time. This may be achieved by giving the copper sleeves 24 a greater exposed surface area than the copper element(s) of a currently available device, while coupling the sleeves 24 with the frame 22 made of a material that is more anodic than the copper elements 24. In this case, the greater amount of available copper is balanced by a slower release rate to achieve, overall, a similar ion release profile. However, in this case, the slower release rate with a larger copper reservoir allows the elution to happen over a potentially longer period of time, thereby extending the effectiveness of the IUD 20 beyond the typical 10 years of device life.

In still other embodiments, the IUD 20 may achieve a copper ion release rate whose release curve is more curvilinear or more linear in comparison to the standard commercial copper IUD release rate curve. In this manner, a metallic IUD with a controlled release rate may be chosen to avoid the burst release of copper ions typically associated with commercial copper IUDs which implement a plastic core. The burst release of copper ions has been shown to be directly associated with the onset of clinical side effects of the standard commercial copper IUDs, including in particular, side effects experienced in the first 1 to 6 months of IUD use, including increased menstrual bleeding, intermenstrual bleeding, cramping and general pelvic pain. Such a reduction in clinical side effects without with the need for ancillary medications would be a significant advantage.

In various embodiments, a method for making the IUD 20 may first involve selecting the wire material for making the metal frame 22 and selecting (or perhaps manufacturing) the copper sleeves 24. The metal frame 22 and/or any other metal structure(s) on IUD 20 may be made from any material with desired galvanic properties, including but not limited to Nitinol, stainless steel, titanium, cobalt-based alloys, tantalum, platinum, gold, silver, and MP35N. The frame 22 may be made from one material or multiple materials. In alternative embodiments, the frame 22 may be made entirely of metal or may have discrete active metallic portions or elements, some or all of which may be in contact with the copper elements 24, with non-metallic parts between the metallic portions or with no parts at all between the metallic portions. The copper elements 24 may take any suitable shape, size, form and number, according to various embodiments. In the embodiment illustrated in FIG. 3, there are ten copper sleeves 24 disposed on the frame 22. Alternative embodiments may include more or fewer sleeves 24 and/or smaller or larger sleeves 24. In other alternative embodiments, the sleeves 24 may be replaced by, or used in combination with, other copper elements, including but not limited to wire, ribbon, coils, tubes, beads, and the like. Additionally, surface processing of the frame 22 and/or other metallic structure may be tailored to achieve a desired galvanic potential. For example, this may be accomplished through heat treatment, oxidation, electropolishing, passivation, and/or other chemical processing.

In some embodiments, the sleeves 24 may be complete tubes. In these embodiments, the sleeves 24 may be passed onto the frame 22 before the frame 22 is bent and twisted to assume its final shape. Alternatively, each sleeve 24 may be a partial tube, and each may include a slit, for example, so that the sleeves 24 can be placed over the frame 22 after the frame 22 has been formed. In some embodiments, some sleeves 24 may be placed over the frame 22 before it is formed into its final shape, and other sleeves 24 may be placed over the frame 22 after it is shaped.

Description of Corrosion Testing

To determine the baseline corrosion behavior of a Nitinol frame and copper sleeves, such as those described above in reference to FIG. 3 (together referred to below as the "ContraMed IUD"), and to evaluate the effects of different surface processing on the Nitinol frame, preliminary potentiodynamic polarization testing was conducted. Processing of the Nitinol surface was targeted to achieve a rest potential ("Erest") similar to or higher than that of the copper sleeves, in order to both optimize the intentional corrosion (and ion release) of the copper and minimize any deleterious galvanic corrosion effects on the Nitinol frame. A review of the literature of electropolished, etched, chemically-polished, and heat-treated (with oxide) Nitinol revealed that rest potentials can be of a wide range, from less than −420 mV to as high as +20 mV vs. SCE.

Potentiodynamic polarization testing was conducted according to ASTM F2129 on copper sleeves and Nitinol frames made from different starting wires and processed in different ways. This testing was conducted in phosphate buffered saline (PBS) at 37° C. at a pH of 7.1. PBS was chosen for this testing for simplicity as well as to allow comparison of the Nitinol corrosion behavior with data from the literature. The testing was conducted using a Gamry Cyclic Polarization Corrosion Apparatus.

Testing was also conducted in simulated uterine fluid (SUF) per the following composition: NaHCO3 0.25; NaH2PO4.2H20 0/072; Glucose 0.50; CaCl2 0.167; KCl0.224; NaCl 4.97. The Simulated Uterine Fluid solution was purged with nitrogen gas, and pH was adjusted to 7.1 before testing. The Rest Potential ("Er") was monitored for one hour before the corrosion test began. Specimens were subjected to a scan from below the zero current potential to 1.0 V at a rate of 1 mV/s. No reverse scan was conducted, and the test was stopped after a scan of −1 mV/s to 0.8 V (vs. Er).

Results

As described previously, the ideal Nitinol surface processing scheme would achieve a rest potential (Erest) that is similar to or higher than that of the copper sleeves (−286.1 mV), in order to both optimize the intentional corrosion (and ion release) of the copper and minimize any deleterious galvanic corrosion effects on the Nitinol frame. At the same time, the Nitinol surface should demonstrate excellent resistance to breakdown. Based on the work of Rosenbloom and Corbett, a Nitinol surface with an average breakdown potential in excess of 600 mV (as tested in PBS at 37° C.) is generally considered to be in an optimum state for use as a medical implant.

Figure 4:
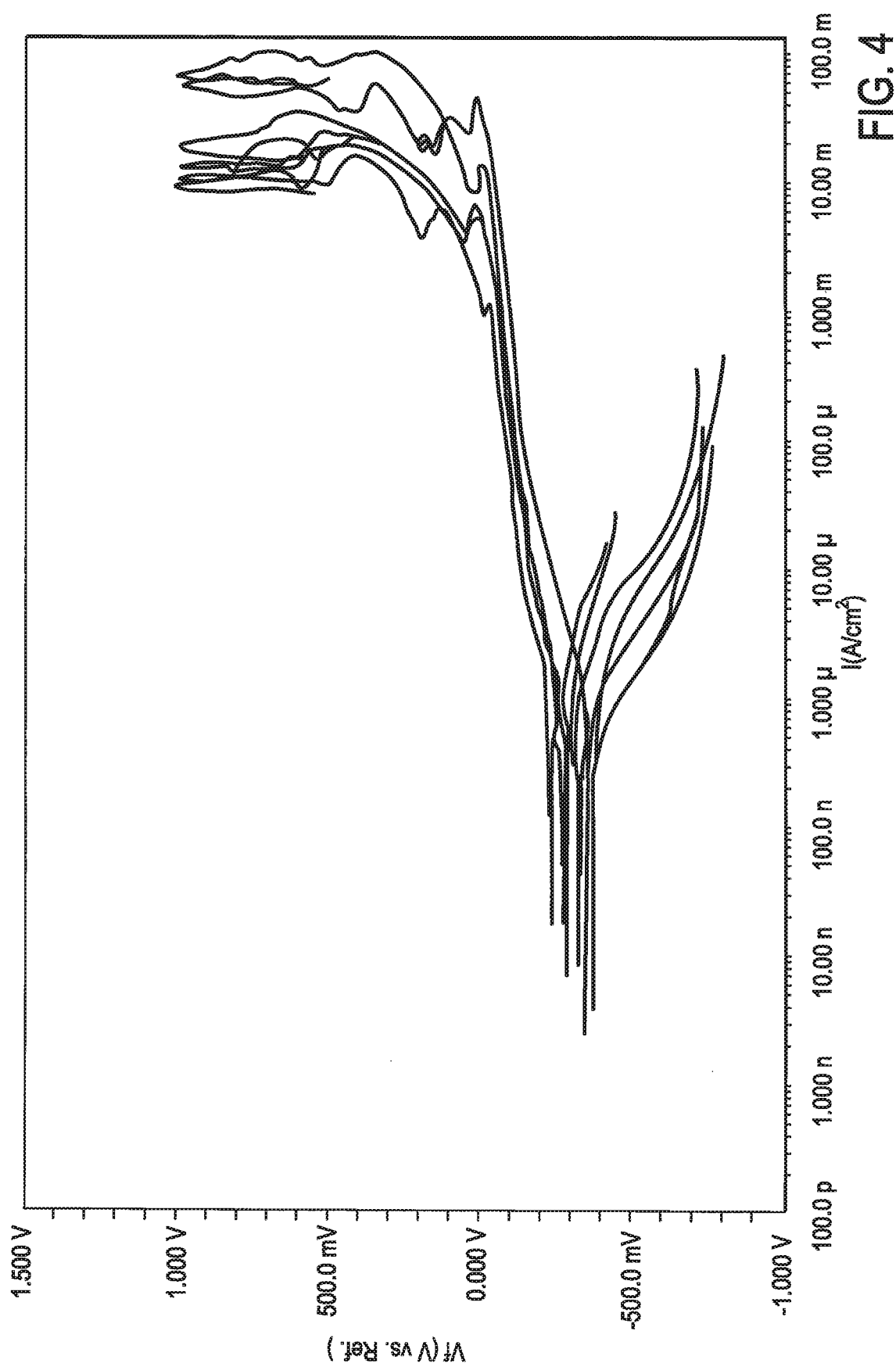
FIG. 4 illustrates potentiodynamic polarization curves for copper sleeves tested in simulated uterine fluid at 37° C., pH=7.1.
Figure 5:
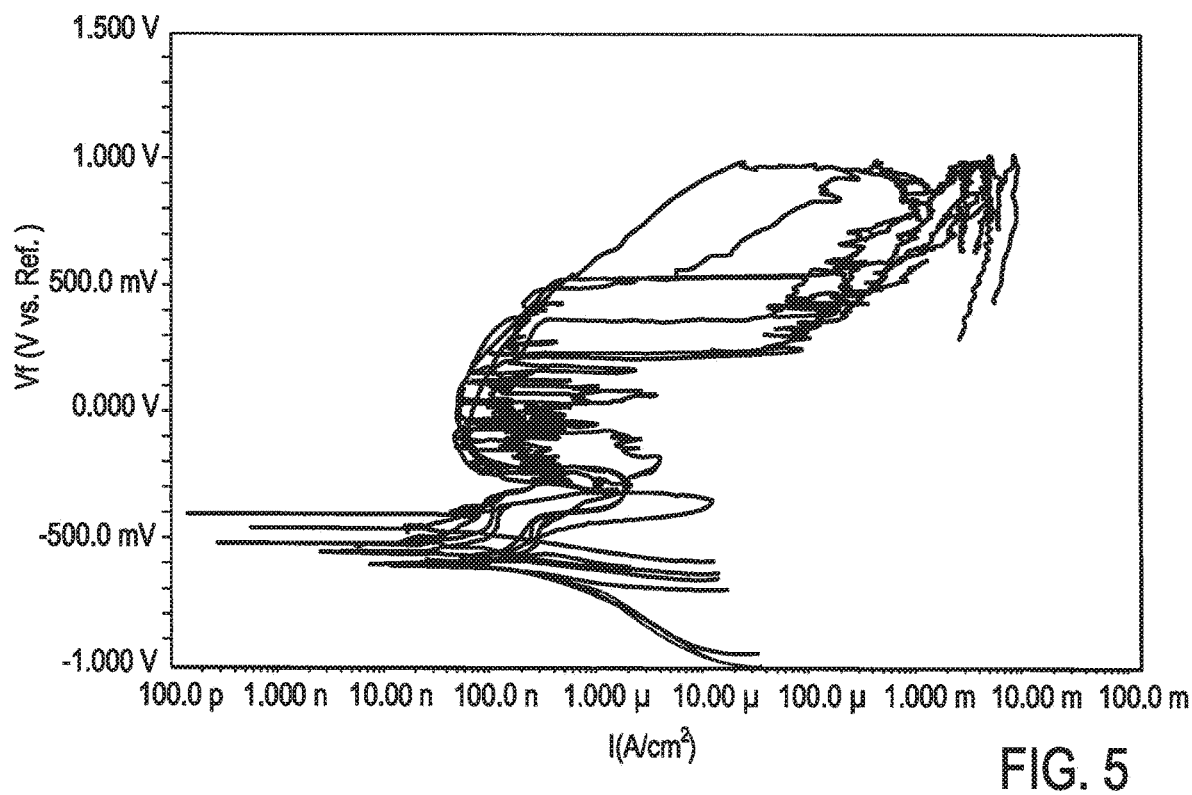
FIG. 5 illustrates potentiodynamic polarization curves for bare Nitinol frames tested in simulated uterine fluid at 37° C., pH=7.1.
Figure 6:
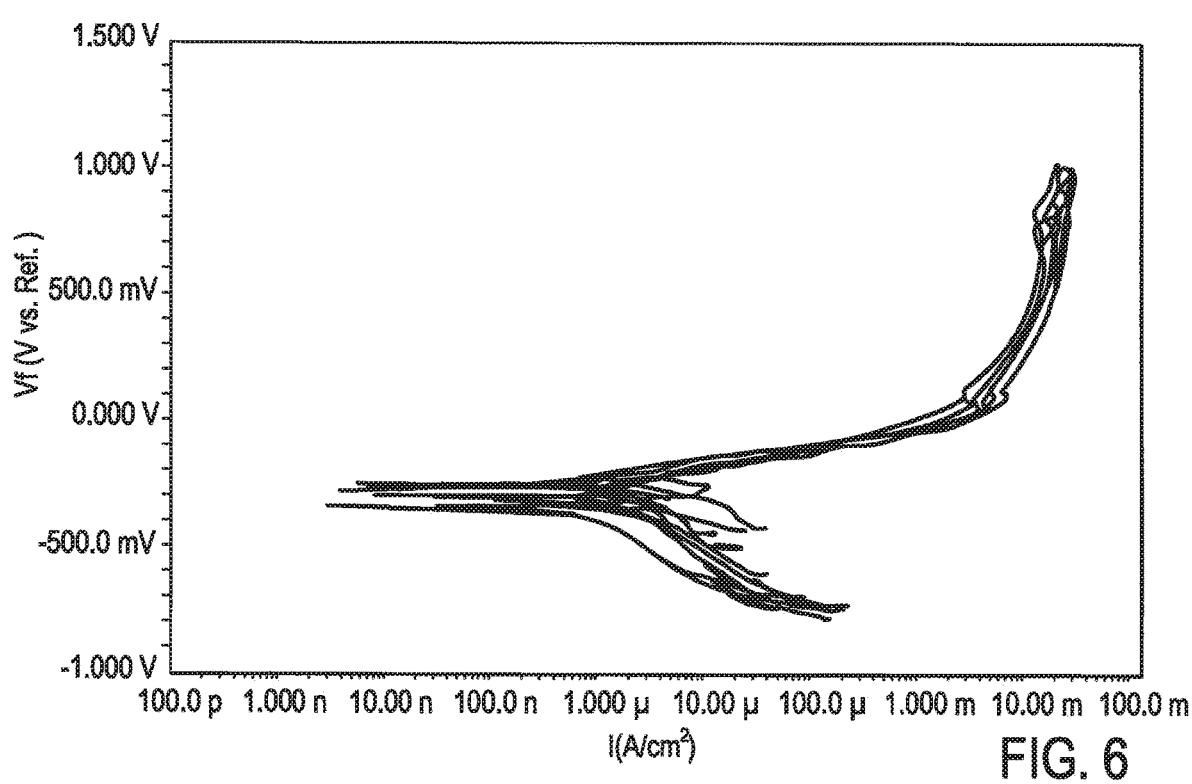
FIG. 6 illustrates potentiodynamic polarization curves for finished device assemblies (copper sleeves crimped onto Nitinol frames) tested in simulated uterine fluid at 37° C., pH=7.1.

FIGS. 4-6 illustrate plots of all the curves for a given sample group on the same axes. FIG. 4 illustrates potentiodynamic polarization curves for copper sleeves tested in simulated uterine fluid at 37° C., pH=7.1. FIG. 5 illustrates potentiodynamic polarization curves for bare Nitinol frames tested in simulated uterine fluid at 37° C., pH=7.1. FIG. 6 illustrates potentiodynamic polarization curves for finished device assemblies (copper sleeves crimped onto Nitinol frames) tested in simulated uterine fluid at 37° C., pH=7.1. As illustrated in FIGS. 4-6, the copper curves and the Nitinol curves are very different. Copper corrodes via generalized corrosion, while Nitinol, due to its formation of a protective surface oxide layer, corrodes via breakdown (i.e., pitting). As expected, the corrosion of the assembled devices is dominated by corrosion of the copper sleeves, and no breakdown behavior is observed in the potentiodynamic polarization curve.

Although various embodiments and features are described herein, the present invention extends beyond the specifically disclosed embodiments to other alternative embodiments and/or uses of the invention and obvious modifications and equivalents thereof. Thus, the scope of the present invention herein disclosed should not be limited by the particular disclosed embodiments described above.

What is claimed is:

1. A method of manufacturing an intrauterine device (IUD) for contraception that has a desired copper elution rate, the method comprising:
   selecting an elongate shape memory member comprising a first metal having a first galvanic potential;
   selecting at least one attachment member comprising a second metal having a second galvanic potential that is different from the first galvanic potential;
   attaching the at least one attachment member to the shape memory member; and
   shaping the shape memory member to form a frame of the intrauterine contraceptive device,
   wherein the first metal and the second metal are specifically selected as materials for the shape memory member and the at least one attachment member, in order to achieve the desired copper elution rate.

2. A method as in claim 1, wherein the shape memory member comprises a wire.

3. A method as in claim 1, wherein the first material is selected from the group consisting of Nitinol, stainless steel, titanium, cobalt-based alloys, tantalum, platinum, gold, silver, and MP35N.

4. A method as in claim 1, wherein the first metal comprises Nitinol, and the second metal comprises copper.

5. A method as in claim 1, wherein the at least one attachment member comprises multiple copper sleeves, and wherein attaching the at least one attachment member to the shape memory member comprises passing the multiple copper sleeves over the shape memory member.

6. A method as in claim 5, further comprising positioning the multiple sleeves along the shape memory member at different positions before or after shaping the shape memory member.

7. A method as in claim 1, wherein the at least one attachment member comprises multiple attachment members selected from the group consisting of sleeves, wires, ribbons, coils, tubes and beads.

8. A method as in claim 1, wherein the first galvanic potential is more anodic than the second galvanic potential.

9. A method as in claim 1, wherein the first galvanic potential is more cathodic than the second galvanic potential.

10. A method as in claim 1, wherein the frame is made entirely of the first metal.

11. A method as in claim 10, wherein the frame comprises a non-rigid material selected from the group consisting of a flexible polymer thread, a polyester thread, a nylon thread or other biocompatible fabric.

12. A method as in claim 1, wherein the frame is made partially of the first metal and partially of a non-metallic substance.

13. A method as in claim 1, further comprising attaching a retrieval string to a bottom portion of the frame.

14. A method as in claim 1, wherein shaping the shape memory member comprises forming the frame to include:
   a bottom loop;
   a middle portion comprising two parts of the elongate shape memory member extending upward from the bottom loop;
   multiple twists in the middle portion, forming a spring portion;
   two bends in the elongate shape memory member at a location above the multiple twists, where the elongate member crosses over itself;
   a first arm extending from a first bend of the two bends;
   a second arm extending from a second bend of the two bends;
   a first end loop at an end of the first arm; and
   a second end loop at an end of the second arm, wherein the first end loop and the second end loop in the elongate shape memory member comprise tissue contact surfaces.

15. A method of manufacturing an intrauterine device (IUD) for contraception that has a desired copper elution rate, the method comprising:
   selecting a wire comprising a first metal having a first galvanic potential;
   selecting at least one attachment member comprising a second metal having a second galvanic potential that is different from the first galvanic potential;

attaching the at least one attachment member to the wire; and shaping the wire to form a frame, comprising:
- a bottom loop;
- a middle portion;
- multiple twists in the middle portion;
- two bends in the elongate shape memory member at a location above the multiple twists in the middle portion, where the elongate member crosses over itself;
- two arms extending from the two bends;
- a first end loop at an end of one of the two arms; and
- a second end loop at an end of the other of the two arms.

16. A method as in claim 15, wherein the first metal comprises Nitinol, and the second metal comprises copper.

17. A method as in claim 15, wherein the at least one attachment member comprises multiple copper sleeves, and wherein attaching the at least one attachment member to the wire comprises passing the multiple copper sleeves over the wire.

18. A method as in claim 17, further comprising positioning the multiple sleeves along the wire at different positions before or after shaping the wire to form the frame.

19. A method as in claim 15, wherein the first galvanic potential is more anodic than the second galvanic potential.

20. A method as in claim 15, wherein the first galvanic potential is more cathodic than the second galvanic potential.

21. An intrauterine device for contraception that has a desired copper elution rate, the intrauterine device comprising:
- an elongate shape memory member comprising a first metal having a first galvanic potential; and
- at least one attachment member attached to the elongate shape memory member and comprising a second metal having a second galvanic potential that is different from the first galvanic potential,
- wherein the first metal and the second metal are specifically selected as materials for the shape memory member and the at least one attachment member, in order to achieve the desired copper elution rate.

22. An intrauterine device as in claim 21, wherein the first metal comprises Nitinol, and the second metal comprises copper.

23. An intrauterine device as in claim 22, wherein the elongate shape memory member comprises a Nitinol wire, and wherein the at least one attachment member comprises multiple copper sleeves disposed over the Nitinol wire.

* * * * *